United States Patent [19]

Fields et al.

[11] Patent Number: 6,096,863
[45] Date of Patent: Aug. 1, 2000

[54] SELF-ASSEMBLING AMPHIPHILES FOR CONSTRUCTION OF PEPTIDE SECONDARY STRUCTURES

[75] Inventors: Gregg B. Fields, Brooklyn Park; Matthew V. Tirrell, St. Paul, both of Minn.

[73] Assignee: Regents of the University of Minnesota, Minneapolis, Minn.

[21] Appl. No.: 08/702,254

[22] Filed: Aug. 23, 1996

[51] Int. Cl.[7] .............................. C07K 7/00; A61K 9/127; C07C 55/00; C07C 69/00
[52] U.S. Cl. .......................... 530/326; 424/417; 424/450; 554/1; 560/1; 530/300
[58] Field of Search ................................... 530/326, 300; 424/417, 450; 554/1; 560/1

[56] References Cited

U.S. PATENT DOCUMENTS

| | | | |
|---|---|---|---|
| 4,732,971 | 3/1988 | DiMarchi et al. | 530/324 |
| 5,117,009 | 5/1992 | Barany | 549/394 |
| 5,196,566 | 3/1993 | Barany et al. | 560/61 |
| 5,366,958 | 11/1994 | Weiner et al. | 514/2 |
| 5,401,511 | 3/1995 | Margalit | 424/450 |
| 5,498,420 | 3/1996 | Edgar et al. | 424/450 |
| 5,576,419 | 11/1996 | Fields | 530/322 |

FOREIGN PATENT DOCUMENTS

| | | | |
|---|---|---|---|
| 0 509 338 | 10/1992 | European Pat. Off. | A61K 9/127 |
| 2 668 365 | 4/1992 | France | A61K 7/48 |
| WO 89/10348 | 11/1989 | WIPO | C07C 99/10 |
| WO 92/14445 | 9/1992 | WIPO | A61K 9/127 |
| WO 92/14446 | 9/1992 | WIPO | A61K 9/127 |

OTHER PUBLICATIONS

Hantke et al, Covalent binding of lipids to protein. Eur. J. Biochem. 34: 284–296, 1973.

McLachlan, A.D., The Double helix coiled coil structure of Murein Lippoprotein from *Escherichia Coli*. J. Mol. Biol. 122,: 493–506, 1978.

Shimizu T, et al, (1989) Enhanced circular dichoism of self–assembled peptidic amphiphiles. Chem.Lett. 8:1341–1344, 1989.

Yu YC, et al, (Jun. 24, 1995) Study of triple–helical structure using peptide–amphiphiles. 14th American peptide symposia 515–516, 1995.

Yu et al., "Study of triple–helical structure using peptide–amphiphiles," *Chemical Abstracts*, 126(1), Abstract No. 8687 (1997).

F. Albericio et al., "Preparation and Application of the 5–(4–(9–Flyorenyl methyloxycarbonyl)aminomethyl–3, 5–dimethoxyphenoxy)–valeric Acid (PAL) Handle for the Solid–Phase Synthesis of C–Terminal Peptide Amides under Mild Conditions", *J. Org. Chem.*, 55, 3730–3743 (1990).

Barany et al., "Solid–phase synthesis: a silver anniversary report", *Int. J. Peptide Protein Res.*, 30, 705–739 (1987).

Barany et al., "Solid–Phase Peptide Synthesis", *The Peptides*, vol. 2, Title Page, Copyright, and Table of Contents (pp. v–viii) (1980).

P. Berndt et al., "Synthetic Lipidation of Peptides and Amino Acids: Monolayer Structure and Properties", *Amer. Chem. Soc.*, 117, 9515–9522 (1995).

Casey, "Protein Lipidation in Cell Signaling", *Science*, 268, 221–225 (1995).

de Bont et al., "A convenient synthesis of a lipopeptide containing a diacylglycerol moiety: preparation of a potential inhibitor of protein kinase C", *Recl. Trav. Chim. Pays–Bas*, 111, 222–226 (1992).

C.G. Fields et al., "Edman Degradation Sequence Analysis of Resin–Bound Peptides Synthesized by 9–Fluorenylmethoxycarbonyl Chemistry", *Peptide Research*, 6, 39–47 (1993).

C.G. Fields et al., "HBTU Activation for Automated Fmoc Solid–Phase Peptide Synthesis", *Peptide Research*, 4, 95–101 (1991).

C.G. Fields et al., "Melanoma Cell Adhesion and Spreading Activities of a Synthetic 124–Residue Triple–helical 'Mini–collagen'",*J. Biol. Chem.*, 268, 14153–14160 (1993).

C.G. Fields et al., "Minimization of Tryptophan Alkylation Following 9–Fluorenylmethoxycarbonyl Solid–Phase Peptide Synthesis", *Tetrahedron Lett.*, 34, 6661–6664 (1993).

C.G. Fields et al., "Purification and Analysis of Synthetic, Triple–Helical 'Minicollagens' by Reversed–Phase High–Performance Liquid Chromatography", *Anal. Biochem.*,231, 57–64 (1995).

C.G. Fields et al., "Solid–Phase Synthesis and Stability of Triple–Helical Peptides Incorporating Native Collagen Sequences", *Biopolymers*, 33, 1695–1707 (1993).

C.G. Fields et al., "Solid–phase synthesis of triple–helical collagen–model peptides", *Lett. Peptide Sci.*, 3, 3–16 (1996).

G.B. Fields, NIH #DK44494 (Abstract Only), Sep. 30, 1992.
G.B. Fields, NIH #AR01929 (Abstract Only), Mar. 1, 1994.
G.B. Fields et al., "Principles and Practice of Solid–Phase Peptide Synthesis", *Synthetic Peptides: A User's Guide* (G.A. Grant, Ed.), W.H. Freeman and Co., N.Y., Chapter 3, pp. 77–183 (1992).

G.B. Fields et al., "Solid phase peptide synthesis utilizing 9–fluorenylmethoxycarbonyl amino acids", *Int. J. Peptide Protein Res.*, 35, 161–214 (1990).

G.B. Fields, "The Collagen Triple–Helix: Correlation of Conformation With Biological Activities", *Connect. Tissue Res.*, 31, 235–243 (1995).

Grab et al., "Promotion of Fibroblast Adhesion by Triple–helical Peptide Models of Type I Collagen–derived Sequences", *J. Biol. Chem.*, 271, 12234–12240 (1996).

Jain et al., "Synthesis of Peptidylglycophospholipids, Novel Derivatives of Muramyl–Dipeptide", *Tetrahedron Lett.*, 22, 2317–2320 (1981).

(List continued on next page.)

*Primary Examiner*—Bennett Celsa
*Assistant Examiner*—Joseph W. Ricigliaw
*Attorney, Agent, or Firm*—Mueting, Raasch & Gebhardt, P.A.

[57] ABSTRACT

A peptide-amphiphile complex having a lipophilic portion and a peptide portion, wherein the peptide portion has a secondary structure.

21 Claims, 3 Drawing Sheets

OTHER PUBLICATIONS

King et al., "A cleavage method which minimizes side reactions following Fmoc solid phase peptide synthesis", *Int. J. Peptide Protein Res.*, 36, 255–266 (1990).

Lauer et al., "Sequence dependence of aspartimide formation during 9–fluorenylmethoxycarbonyl solid–phase peptide synthesis", *Lett. Peptide Sci.*, 1, 197–205 (1994).

Merrifield, "Solid Phase Peptide Synthesis. I. The Synthesis of a Tetrapeptide", *J. Am. Chem. Soc.*, 85, 2149–2154 (1963).

Miles et al., "Promotion of Cell Adhesion by Single–stranded and Triple–helical Peptide Models of Basement Membrane Collagen α1(IV)531–543", *J. Biol. Chem.*, 269, 30939–30945 (1994).

Morton et al., "Platelet Aggregation by a Collagen–Like Synthetic Peptide", *Thrombosis Res.*, 72, 367–372 (1993).

W. Prass et al., "Lipopeptides of the N–terminus of *Escherichia coli* lipoprotein: synthesis, mitogenicity and properties in monolayer experiments", *Biochim. et Biophys. Acta*, 900, 116–128 (1987).

Rao et al., "Promotion of Human Platelet Adhesion and Aggregation by a Synthetic, Triple–helical 'Mini–collagen'", *J. Biol. Chem.*, 269, 13899–13903 (1994).

M.B. Sankaram, "Membrane Interaction of Small N–Myristoylated Peptides: Implications for Membrane Anchoring and Protein–Protein Association", *J. Biophys.*, 67, 105–112 (1994).

T. Shimizu et al., "Self–assembling properties of synthetic peptidic lipids", *Biochem. et Biophys. Acta*, 1147, 50–58 (1993).

Thompson et al., "Covalent Linkage of a Synthetic Peptide to a Fluorescent Phospholipid and Its Incorporation Into Supported Phospholipid Monolayers", *Biochim. Biophys. Acta.*, 772, 10–19 (1984).

Y. Yu et al., "Self–Assembling Amphiphiles for Construction of Protein Molecular Architecture", *J. Amer. Chem. Soc.*, 118, 12515–12520 (1996).

SELF-ASSEMBLING AMPHIPHILES FOR CONSTRUCTION OF PEPTIDE SECONDARY STRUCTURES

STATEMENT OF GOVERNMENT RIGHTS

This invention was made with government support under Grant No. DK44494 and AR01929, awarded by the National Institutes of Health. The government has certain rights in the present invention.

BACKGROUND OF THE INVENTION

Biomolecules, such as proteins, are remarkable in their capability to self-assemble into well-defined and intricate structures. The most intriguing self-assembly process is the folding of peptide chains into native protein structures. The fundamental building blocks in proteins are not simple canonical secondary structures (such as α-helices and β-sheets), but characteristic assemblies of secondary structural elements. Among the protein assemblies are the simple β/α/β motif, the hairpin, and the α-helical coiled-coil, as well as the more complicated four α-helical bundle, the doubly wound β-sheet, the Jelly roll, and the Greek key.

Many researchers have attempted to create protein-like assemblies for the purpose of studying protein folding, and to create new biomaterials for use in medical devices and other medical applications such as drug delivery systems. The most common assembly used for protein design is the four α-helical bundle, which has been developed as a synthetic enzyme, for redox catalysis, for antibody production, as ion channels in lipid bilayers, and as surface mimetics of human class I MHC. The collagen-model triple-helix has also been used for protein design. Synthetic triple-helical proteins have incorporated native type IV collagen sequences that promote adhesion and spreading of tumor cells and native type III or IV collagen sequences that induce the aggregation of platelets. See, for example, Fields et al., *J. Biol. Chem.*, 268, 14153–14160 (1993); Miles et al., *J. Biol. Chem.*, 269, 30939–30945 (1994); Grab et al., *J. Biol. Chem.*, 271, 12234–12240 (1995); Morton et al., *Thrombosis Res.*, 72, 367–372 (1993); and Rao et al., *J. Biol. Chem.*, 269, 13899–13903 (1994).

The triple-helix is a super-secondary structure characteristic of collagen. Collagen-like triple-helices are also found in macrophage scavenger receptors types I and II and bacteria-binding receptor MARCO, complement component C1q, pulmonary surfactant apoprotein, acetylcholinesterase, and mannose binding protein. The triple-helix consists of three polypeptide chains, each in an extended, left-handed polyPro II-like helix, which are staggered by one residue and then supercoiled along a common axis in a right-handed manner. Geometric constraints of the triple-helical structure require that every third amino acid is Gly, resulting in a Gly-X-Y repeating sequence. Stability of the triple-helix depends upon the imino acid content. Furthermore, hydroxyproline (Hyp) stabilizes the triple-helical structure by facilitating the formation of a hydrogen bonding network with surrounding water molecules. For simple collagen-model peptides, (Gly-Pro-Hyp)$_n$ forms the most thermally stable triple-helices, with a melting temperature ($T_m$) of 58–60° C. when n=10 (SEQ. ID NO:3).

Several strategies have been employed in order to induce triple-helical structure formation in isolated collagen ligand sequences. See, for example, Fields, *Connect. Tissue Res.*, 31, 235–243 (1995). Simply adding a number of Gly-Pro-Hyp repeats to both ends of a collagenous sequence can, under certain circumstances, induce triple-helical conformation. However, even with more than 50% of the peptide sequence consisting of Gly-Pro-Hyp repeats, the resulting triple-helices still may not have sufficient thermal stability ($T_m$<37° C.) to survive physiological conditions. Substantial stabilization of the triple-helical structure can be achieved with the introduction of covalent links between the C-terminal regions of the three peptide chains. See, for example, Fields et al., *J. Biol. Chem.*, 268, 14153–14160 (1993); Grab et al., *J. Biol. Chem.*, 271, 12234–12240 (1995); Fields et al., *Biopolymers*, 33, 1695–1707 (1993); Fields et al., *Lett. Peptide Sci.*, 3, 3–16 (1996); and Fields et al., *Anal. Biochem.*, 231, 57–64 (1995). However, the large size (90–125 amino acid residues) of the resulting "branched" triple-helical peptide compounds make them difficult to synthesize and purify. Ideally, one would like to create a system by which synthetic linear peptide chains self-assemble into desirable secondary structures (including super-secondary structures).

Thus, what is still needed are complexes of synthetic linear peptide chains that self-assemble into secondary structures. Specifically, what is needed are approaches to building a collagen-like structural motif that facilitate peptide alignment and structure initiation and propagation.

SUMMARY OF THE INVENTION

The present invention provides a peptide-amphiphile complex comprising a lipophilic portion and a peptide portion, wherein the peptide portion has a secondary structure. Preferably, the peptide portion comprises a cell recognition site. Preferably, the secondary structure is an α-helix or β-sheet, or a super-secondary structure, such as a collagen-like triple helix, a β/α/β motif, a hairpin, and an α-helical coiled-coil. More preferably, the secondary structure is the super-secondary structure collagen-like triple helix. Preferably, the peptide secondary structure is stable under physiological conditions (i.e., pH=7.4 and temperature=35° C.). More preferably, the melting temperature of the peptide portion is at least about 36° C.

Preferably, the lipophilic portion comprises two linear alkyl chains and a trifunctional amino acid. More preferably, each alkyl chain has up to about 20 carbon atoms and the trifunctional amino acid is glutamate (Glu).

Preferably, the peptide portion includes no greater than about 25 amino acid residues. More preferably, the peptide portion comprises a collagen-like sequence or an alpha-helical forming sequence. Most preferably, the peptide portion comprises the α1(IV)1263–1277 collagen sequence Gly-Val-Lys-Gly-Asp-Lys-Gly-Asn-Pro-Gly-Trp-Pro-Gly-Ala-Pro (SEQ. ID NO:1). The peptide portion can optionally include one or more structure-inducing sequences, such as Gly-Pro-Hyp repeats and Gly-Pro-Pro repeats.

The peptide-amphiphile complex can be in the form of a vesicle, such as a liposome, or it can be in the form of a micelle. These can be used as drug delivery devices for targeted cells.

The present invention also provides a peptide-amphiphile complex comprising a lipophilic portion and a peptide portion, wherein the peptide portion has a secondary structure, the complex having the following structure:

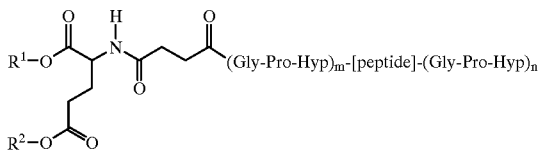

wherein: $R^1$ and $R^2$ are each independently $C_{10}$–$C_{20}$ hydrocarbyl groups (preferably $C_{12}$–$C_{16}$ hydrocarbyl groups); m=0–4 and n=0–4 (preferably with the proviso that at least one of m or n is 4); and the [peptide] refers to a collagen-like sequence or an alpha-helical forming sequence (preferably, the α1(IV)1263–1277 collagen sequence Gly-Val-Lys-Gly-Asp-Lys-Gly-Asn-Pro-Gly-Trp-Pro-Gly-Ala-Pro (SEQ. ID NO:1). In the above formula, the "peptide portion" includes the optional Gly-Pro-Hyp sequences and the [peptide] sequences.

DETAILED DESCRIPTION OF THE INVENTION

Figure 1:
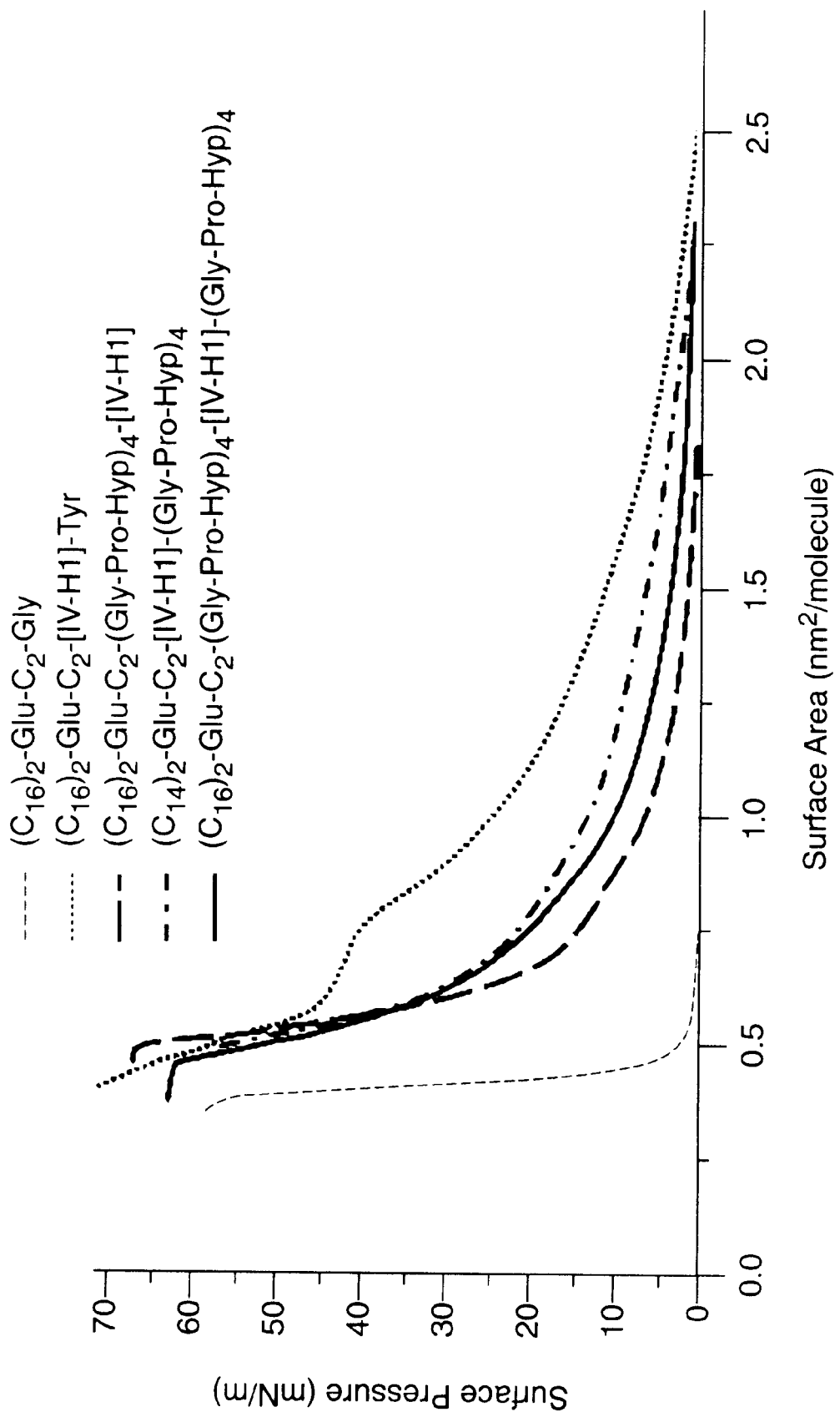
FIG. 1. Surface pressure-area isotherms of collagen-model peptide-amphiphiles. All peptide-amphiphile isotherms converge at surface pressure values of above 50 mN/m at a surface area of 0.6 nm$^2$/molecule. This surface area is different from the exclusion volume (0.4 nm$^2$/molecule) for a dialkyl chain amphiphile molecule [e.g. $(C_{16})_2$-Glu-$C_2$-Gly].

The present invention provides a peptide-amphiphile complex comprising a lipophilic portion (e.g., tail) and a peptide portion (e.g., head group), wherein the peptide portion has a secondary structure. Although lipidated peptides and proteins are known [see, for example, Jain et al., Tetrah edron Lett. 22, 2317–2320 (1981); Thompson et al., Biochim. Biophys. Acta, 772, 10–19 (1984); and Casey, Science, 268, 221–225 (1995)], none have been shown to display secondary structure.

The peptide portion preferably contains a biological function, such as a cell recognition site, and optionally one or more structure-inducing sequences. The liphophilic portion typically does not detract from the structure of the peptide portion, and it may enhance and/or stabilize the structure of the peptide portion. In some situations, it may even facilitate or induce the structure formation by aligning the peptide strands, as well as provide a hydrophobic surface for self-association (i.e., association without the formation of covalent bonds) and/or interaction with other surfaces. Thus, the lipophilic portion is also capable of forming a lipid-like structure, such as a micelle.

When placed in an aqueous environment, the amphiphilic character (i.e., hydrophobic tail and hydrophilic head group) of these complexes facilitates peptide alignment and structure initiation and propagation at the lipid-solvent interface. Thus, the complexes of the present invention are advantageous because they can noncovalently self-assemble to form a stable secondary (preferably, collagen-like triple helical) structural motif.

The peptide portions of the peptide-amphiphile complexes described herein form secondary structures. Herein, a "secondary structure" includes simple secondary structural elements, such as α-helices and β-sheets, as well as assemblies of secondary structural elements (i.e., super-secondary structures or motifs), such as collagen-like triple helices, β/α/β motifs, hairpins, α-helical coiled-coils, etc.

Significantly, these structural elements are preferably stable, primarily due to optional internal structure-inducing sequences and/or stabilizing hydrophobic interactions of the lipophilic tail. As used herein, a "stable" structural element is one that withstands physiological conditions without substantially losing its structure. This stability can be represented by the melting temperature of the peptide portion, which is preferably at least about 36° C. Significantly, this stability occurs without the need for covalent links, for example, between the C-terminal regions of three peptide chains.

The lipophilic portion can be any organic group having at least two long alkyl groups (preferably, linear chains) that are capable of forming lipid-like structures. This organic group also includes suitable functional groups for attachment to the peptide portion. Preferably, the lipophilic portion is a branched group having two linear alkyl chains, each having up to about 20 carbon atoms in each chain. These alkyl chains are typically attached to the peptide portion through a linker group having suitable functionality such as ester groups, amide groups, and combinations thereof. Suitable lipophilic portions can be derived from compounds such as, for example, dialkylamines, dialkylesters, and phospholipids. Preferably, they are derived from dialkylesters. More preferably, the lipophilic portions of the complexes of the present invention have two $C_{10}$–$C_{20}$ alkyl chains, which are attached to the peptide portion through a linker, such as a trifunctional amino acid. Typically, the linker is glutamate.

The peptide portion can be derived from any peptide (oligopeptide, polypeptide, or protein) that is capable of forming a specific structural element, to form the complexes of the present invention. Preferably, the peptide portion has biological activity, such as cell recognition activity, enzymatic activity, etc. The peptide portion can include a wide variety of amino acid residues in a wide variety of lengths, as long as the peptide portion is not so long that it detracts from the lipophilic portion forming a lipid-like structure such as a micelle. Preferably, the peptide portion includes no greater than about 25 amino acid residues, and more preferably about 15–18 amino acid residues. Examples include, but are not limited to, the α1(IV)1263–1277 collagen sequence Gly-Val-Lys-Gly-Asp-Lys-Gly-Asn-Pro-Gly-Trp- Pro-Gly-Ala-Pro (herein referred to as [IV-H1] or SEQ. ID NO:1) and other collagen-like sequences (i.e., sequences having Gly-x-y repeats), as well as alpha-helical forming sequences.

The peptide portion can optionally contain one or more structure-inducing sequences, although they are not necessarily required. In some situations, such structure-inducing sequences may provide greater stability to the peptide portions of the complexes of the present invention. Examples include Gly-Pro-Hyp repeats, Gly-Pro-Pro repeats, and the like. Preferably, the structure-inducing sequences are capable of inducing triple helical structures.

A preferred class of peptide-amphiphile complexes is exemplified by a long chain dialkylester lipophilic (i.e., lipid) tail bonded to a peptide head group of the following formula:

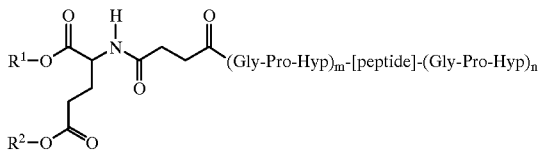

wherein: $R^1$ and $R^2$ are each independently $C_{10}$–$C_{20}$ hydrocarbyl groups (preferably, $C_{12}$–$C_{16}$ hydrocarbyl groups); m=0–4 and n=0–4 (preferably, at least one of m or n is 4); and [peptide] refers to a collagen-like sequence or an alpha-helical forming sequence (preferably, a collagen-like sequence). More preferably, the [peptide] is the α1(IV) 1263–1277 collagen sequence Gly-Val-Lys-Gly-Asp-Lys-Gly-Asn-Pro-Gly-Trp-Pro-Gly-Ala-Pro (SEQ. ID NO:1), which is known to promote melanoma cell adhesion and spreading. Using this peptide, the lipid assists in creating a collagen-like peptide-amphiphile. The resultant peptide-amphiphile complex also promotes cell adhesion and spreading.

The complexes of the present invention can be made by a variety of solid-phase or solution techniques. For example, although the peptides can be prepared by other methods (e.g., solution methods) and then attached to a support material for subsequent coupling with the lipid, it is preferred that standard solid-phase organic synthesis techniques, such as solid-phase peptide synthesis (SPPS) techniques be used. That is, a peptide can be synthesized, subsequently attached to a support material, coupled with a lipid, and then removed from the support material using a variety of techniques. Preferably, however, the peptide is synthesized on a support material, coupled with the lipid, and then removed from a support material using a variety of techniques.

For the preparation of peptides (oligopeptides, polypeptides, or proteins), solid-phase peptide synthesis involves a covalent attachment step (i.e., anchoring) that links the nascent peptide chain to a support material (typically, an insoluble polymeric support) containing appropriate functional groups for attachment. Subsequently, the anchored peptide is extended by a series of addition (deprotection/coupling) cycles that involve adding $N^\alpha$-protected and side-chain-protected amino acids stepwise in the C to N direction. Once chain assembly has been accomplished, protecting groups are removed and the peptide is cleaved from the support. Typically, the lipid is added to the peptide before the protecting groups are removed.

Typically, SPPS begins by using a handle to attach the initial amino acid residue to a functionalized support material. A handle (i.e., linker) is a bifunctional spacer that, on one end, incorporates features of a smoothly cleavable protecting group, and on the other end, a functional group, often a carboxyl group, that can be activated to allow coupling to the functionalized support material. Known handles include acid-labile p-alkoxybenzyl (PAB) handles, photolabile o-nitrobenzyl ester handles, and handles such as those described by Albericio et al., *J. Org. Chem.*, 55, 3730–3743 (1990) and references cited therein, and in U.S. Pat. Nos. 5,117,009 (Barany) and 5,196,566 (Barany et al.).

For example, if the support material is prepared with amino-functional monomers, typically, the appropriate handles are coupled quantitatively in a single step onto the amino-functionalized supports to provide a general starting point of well-defined structures for peptide chain assembly. The handle protecting group is removed and the C-terminal residue of the $N^\alpha$-protected first amino acid is coupled quantitatively to the handle. Once the handle is coupled to the support material and the initial amino acid or peptide is attached to the handle, the general synthesis cycle proceeds. The synthesis cycle generally consists of deprotection of the $N^\alpha$-amino group of the amino acid or peptide on the support material, washing, and, if necessary, a neutralization step, followed by reaction with a carboxyl-activated form of the next $N^\alpha$-protected amino acid. The cycle is repeated to form the peptide of interest. Solid-phase peptide synthesis methods using functionalized insoluble support materials are well known. See, for example, Merrifield, *J. Am. Chem. Soc.*, 85, 2149 (1963); Barany and Merrifield, In *Peptides*, Vol. 2, pp. 1–284 (1979); Barany et al., *Int. J. Peptide Protein Res.*, 30, 705–739 (1987); Fields et al., In *Synthetic Peptides: A User's Guide* (G. A. Grant, Ed.), Chapter 3, pp. 77–183, W.H. Freeman and Co., N.Y. (1992); and Fields et al., *Int. J. Peptide Protein Res.*, 35, 161–214 (1990).

When SPPS techniques are used to synthesize the peptides on the support material, Fmoc methodologies are preferably used. This involves the use of mild orthogonal techniques using the base-labile $N^\alpha$-9-fluorenylmethyloxycarbonyl (Fmoc) protecting group. Fmoc amino acids can be prepared using fluorenylmethyl succinimidyl carbonate (Fmoc-OSu), Fmoc chloride, or [4-(9-fluorenylmethyloxycarbonyloxy)phenyl]dimethylsulfonium methyl sulfate (Fmoc-ODSP). The Fmoc group can be removed using piperidine in dimethylformamide (DMF) or N-methylpyrrolidone, or using 1,8-diazabicyclo[5.4.0]undec-7-ene (DBU) in DMF. After Fmoc removal, the liberated $N^\alpha$-amine of the supported resin is free and ready for immediate attachment of the lipid without an intervening neutralization step. The immobilized amphiphilic analog of the desired peptide can then be removed, for example, using trifluoroacetic acid (TFA) at room temperature. Such Fmoc solid-phase peptide synthesis methodologies are well known to one of skill in the art and are discussed in Fields et al., In *Synthetic Peptides: A User's Guide* (G. A. Grant, Ed.), Chapter 3, pp. 77–183, W.H. Freeman and Co., N.Y. (1992); and Fields et al., *Int. J. Peptide Protein Res.*, 35, 161–214 (1990).

A variety of support materials for preparation of the complexes of the present invention can be used. They can be of inorganic or organic materials and can be in a variety of forms (e.g., membranes, particles, spherical beads, fibers, gels, glasses, etc.). Examples include, porous glass, silica, polystyrene, polyethylene terephthalate, polydimethylacrylamides, cotton, paper, and the like. Examples of suitable support materials are described by Fields et al., *Int. J. Peptide Protein Res.*, 35, 161–214 (1990); and *Synthetic Peptides: A User's Guide* (G. A. Grant, Ed.), Chapter 3, pp. 77–183, W.H. Freeman and Co., N.Y. (1992). Functionalized polystyrene, such as amino-functionalized polystyrene, aminomethyl polystyrene, aminoacyl polystyrene, p-methylbenzhydrylamine polystyrene, or polyethylene glycol-polystyrene resins can be used for this purpose.

The peptide-amphiphile complexes described herein provide a simple and general approach for building stable protein structural motifs using peptide head groups. One of the most intriguing features of this system is the possible formation of stable lipid films on solid substrates, or the use of the novel amphiphiles in bilayer membrane systems, where the lipid tail serves not only as peptide structure inducing agent but also as anchor of the functional head group to the lipid assembly. In general, the present peptide-amphiphiles may form a great variety of structures in solution including micelles and vesicles. They can also be mixed with vesicle-forming lipids, such as dilauryl phosphatidylcholine, to form stable mixed vesicles with collagen-model, triple-helical peptide head groups. For example, a drug targeting system against melanoma cells can be designed using vesicles containing the [IV-H1] (SEQ ID NO:1) peptide-amphiphile.

The invention will be further described by reference to the following detailed examples. These examples are offered to further illustrate the various specific and illustrative embodiments and techniques. It should be understood, however, that many variations and modifications may be made while remaining within the scope of the present invention.

EXAMPLES

Materials and Methods
Preparation of Peptide-Amphiphiles

The dialkyl ester lipophilic tail precursors 1',3'-dihexadecyl N-[O-(4-nitrophenyl)succinyl]-L-Glu [designation $(C_{16})_2$-Glu-$C_2$-pNp], 1',3'-ditetradecyl N-[O-(4-nitrophenyl)succinyl]-L-Glu [designation $(C_{14})_2$-Glu-$C_2$-pNp], and 1',3'-didodecyl N-[O-(4-nitrophenyl)succinyl]-L-Glu [designation $(C_{12})_2$-Glu-$C_2$-pNp] were synthesized according to the following procedure described for the preparation of 1',3'-dihexadecyl N-[O-(4-nitrophenyl) succinyl]-L-Glu. The $C_{14}$ and $C_{12}$ tails were prepared using 1-tetradecyl alcohol and 1dodecyl alcohol in place of hexadecanol, respectively.

Hexadecanol (44.85 g, 0.185 mol) and Glu (13.6 g, 0.092 mol) were mixed with 21.0 g (0.102 mol) of p-toluenesulfinate in toluene, and the mixture was heated until an equimolar amount of water was recovered in a Dean-Stark trap. The toluene was removed, and the product (1',3'-dihexadecyl-L-glutamate) recrystallized from acetone. TLC (silica gel K60, methanol(1)chloroform(99)): $R_f$0.3 (product), 0.05 (free amine). This product (20 g, 26 mmol) was dissolved in a 1:1 THF:CHCl$_3$ mixture along with triethylamine (5.5 ml, 39 mmol). Succinic anhydride (3.9 g, 39 mmol) was added with stirring. The mixture was kept for 4 hours at 30° C. The product (1',3'-dihexadecyl N-succinyl-L-glutamate) obtained after removal of the solvent was recrystallized from acetone and ethanol. TLC (silica gel K60, methanol(4):chloroform(96)): $R_f$0.4 (product). This product (6.90 g, 9.9 mmol) and p-nitrophenol (1.65 g, 11.9 mmol) were dissolved in CH$_2$Cl$_2$, and 2.05 g (9.9 mmol) of N,N-dicyclohexylcarbodiimide as well as a catalytic amount (80 g) of (dimethylamino)pyridine was added to the reaction mixture on an ice bath. The reaction was continued for 2 hours on the ice bath and for 24 hours at room temperature. The formed dicyclohexylurea was filtered off, and the reaction product (1',3'-dihexadecyl N-[O-(4-nitrophenyl) succinyl]-L]glutamate) was precipitated with cold dry ethanol. TLC (silica gel K60, methanol(5):chloroform(95)): $R_f$0.7 (product).

All standard peptide synthesis chemicals and solvents were analytical reagent grade or better and purchased from applied Biosystems, Inc. (Foster City, Calif.) or Fisher Scientific (Pittsburgh, Pa.). Fmoc-4-(2',4'-dimethoxyphenylaminomethyl)phenoxy resin (substitution level=–0.46 mmol/g) was purchased from Novabiochem (La Jolla, Calif.). All Fmoc-amino acid derivatives were from Novabiochem or Millipore Corp. and were of L-configuration. 1-Hydroxybenzotriazole (HOBt) was purchased from Novabiochem, 2-(1H-benzotriazole-1-yl)-1,1,3,3-tetramethyluronium hexafluorophosphate (HBTU) from Richelieu Biotechnologies (St. Hyacinthe, Quebec), and N,N-diisopropylethylamine (DIEA) from Fisher Scientific.

Peptide-resin assembly was performed by Fmoc solid-phase methodology on an ABI 431A Peptide Synthesizer as discussed in Fields et al., *Int. J. Peptide Protein Res.*, 35, 161–214 (1990); Fields et al., *Peptide Res.*, 4, 95–101 (1991); Lauer et al., *Lett. Peptide Sci.*, 1, 197–205 (1995); and Fields et al., *Peptide Res.*, 6, 39–47 (1993). Peptide-resins were characterized by Edman degradation sequence analysis as described for "embedded" (noncovalent) sequencing in Fields et al., *Peptide Res.*, 6, 39–47 (1993). Peptide-resins were either cleaved or lipidated with the appropriate $(C_n)_2$-Glu-$C_2$ tail and then cleaved.

For example, N-dihexadecyl N-[1-(N-peptidyl)succinyl]-L-glutamates were synthesized by incubation of the appropriate NH$_2$-peptidyl-resin (obtained after incubation of the fully protected Fmoc-peptidyl resin for 20 minutes in piperidine/dimethylformamide (1:4) and washing with DMF) with 4-fold molecular excesses of N-dihexadecyl N-[O-(4-nitrophenyl)-succinyl]-L-glutamate and 1-hydroxybenzotriazole over the substitution level of the resin in a DMF(1):CH$_2$Cl$_2$(1) mixture.

Cleavage and side-chain deprotection of peptide-resins and peptide-amphiphile-resins proceeded, for example, for 1 hour using either ethanedithiol-thioanisole-phenol water TFA (2.5:5:5:5:82.5) or water-TFA (1:19) as described by King et al., *Int. J. Peptide Protein Res.*, 36, 255–266 (1990); and Fields et al., *Tetrahedron Lett.*, 34, 6661–6664 (1993). Peptide-amphiphile cleavage solutions were not extracted with methyl tBu ether prior to purification.

Peptides and peptide-amphiphiles were purified using reversed-phase high performance liquid chromatography (RP-HPLC) on a Rainin AutoPrep System. Peptides were purified with a Vydec 218TP152022 $C_{18}$ column (15–20 µm particle size, 300 Angstrom pore size, 250×25 mm) at a flow rate of 5.0 ml/minute. The elution gradient was either 0–60% B or 0–100% B in 60 minutes, where A was 0.1% TFA in water and B was 0.1% TFA in acetonitrile. Detection was at 229 nm. Peptide-amphiphile purification was achieved using a Vydac 214TP152022 $C_4$ column (15–20 µm particle size, 300 Angstrom pore size, 250×22 mm) at a flow rate of 10 ml/minute. The elution gradient was 55–90% B in 20 minutes, where A was 0.05% TFA in water and B was 0.05% TFA in acetonitrile. Detection was at 229 nm. Analytical RP-HPLC was performed on a Hewlett-Packard 1090 Liquid Chromatograph equipped with a Hypersil $C_{18}$ column (5 µm particle size, 120 Angstrom pore size, 200×2.1 mm) at a flow rate of 0.3 ml/minute. The elution gradient was 0–60% B in 45 minutes, where A and B were the same as for peptide purification. Diode array detection was at 220, 254, and 280 nm.

Purity and composition of the final compounds was assured by Edman degradation sequence analysis of the peptides and analytical RP-HPLC and laser desorption mass spectrometry (LDMS) of the peptides and peptide-amphiphiles. Edman degradation sequence analysis was performed on an Applied Biosystems 477A Protein Sequencer/120A Analyzer. LDMS was performed on a Hewlett Packard matrix-assisted laser desorption time-of-flight mass spectrometer. FABMS was performed on a VG 7070E-HP with a glycerol matrix.

The following [M+H]$^+$ values for peptides and peptide-amphiphiles were obtained: [IV-H1] (SEQ ID NO:1), 1436.8 Da (theoretical 1436.6 Da); (Gly-Pro-Hyp)$_4$-[IV-H1] (SEQ ID NO:2-SEQ ID NO:1), 2502.5 Da (theoretical 2502.7 Da); [IV-H1]-(Gly-Pro-Hyp)$_4$ (SEQ ID NO:1-SEQ ID NO:2), 2502.6 Da (theoretical 2502.7 Da); (Gly-Pro-Hyp)$_4$-[IV-H1]-(Gly-Pro-Hyp)$_4$ (SEQ ID NO:2-SEQ ID NO:1-SEQ ID NO:2), 3574.2 Da (theoretical 3574.9 Da); (C$_{16}$)$_2$-Glu-C$_2$-[IV-H1]-Tyr ((C$_{16}$)$_2$-Glu-C$_2$-SEQ ID NO:1-Tyr), 2277.2 Da (theoretical 2278.4 Da); (C$_{16}$)$_2$-Glu-C$_2$-(Gly-Pro-Hyp)$_4$-[IV-H1] ((C$_{16}$)$_2$-Glu-C$_2$-SEQ ID NO:2-SEQ ID NO:1), 3184.6 Da (theoretical 3183.8 Da); (C$_{14}$)$_2$-Glu-C$_2$-[IV-H1]-(Gly-Pro-Hyp)$_4$ ((C$_{14}$)$_2$-Glu-C$_2$-SEQ ID NO:1-SEQ ID NO:2), 3130.8 Da (theoretical 3127.8 Da); (C$_{12}$)$_2$-Glu-C$_2$-[IV-H1] ((C$_{12}$)$_2$-Glu-C$_2$-SEQ ID NO:1), 2003.6 Da (theoretical 2002.6 Da); (C$_{12}$)$_2$-Glu-C$_2$-(Gly-Pro-Hyp)$_4$-[IV-H1] ((C$_{12}$)$_2$-Glu-C$_2$-SEQ ID NO:2-SEQ ID NO:1), 3075.8 Da (theoretical 3071.8 Da); (C$_{12}$)$_2$-Glu-C$_2$-[IV-H1]-(Gly-Pro-Hyp)$_4$((C$_{12}$)$_2$-Glu-C$_2$-SEQ ID NO:1-SEQ ID NO:2), 3076.9 Da (theoretical 3071.8 Da). For the (C$_{12}$)$_2$-Glu-C$_2$-(Gly-Pro-Hyp)$_4$-[IV-H1]-(Gly-Pro-Hyp)$_4$ ((C$_{12}$)$_2$-Glu-C$_2$-SEQ ID NO:2-SEQ ID NO:1-SEQ ID NO:2) peptide-amphiphile, [M+Na]$^+$=4166.8 Da (theoretical 4162.9 Da).

Pressure-Area Isotherms

All isotherms were obtained at 22° C. after spreading a peptide amphiphile solution in hexane-CHCl$_3$-methanol (5:4:1) over a pure water subphase. After 15 minutes, the monolayer was compressed laterally with constant speed for 10 mm/minute on a computerized KSV LB5000 Langmuir-Blodgett instrument and surface pressure detected using film balance with a platinum Wilhemy plate.

Circular Dichroism Spectroscopy

Spectra were recorded on a JASCO J-710 spectropolarimeter using a thermostated 0.1 mm quartz cell. Thermal transition curves were obtained by recording the molar ellipticity ([θ]) in the range of 10–80° C. at λ=225 nm. The peptide and peptide-amphiphile concentrations were 0.5 mM in H$_2$O at 25° C.

NMR Spectroscopy

Freeze-dried samples for NMR spectroscopy were dissolved in D$_2$O or D$_2$O—H$_2$O (1:9) at peptide and peptide-amphiphile concentrations of 3–5 mM. NMR spectra were acquired on a 500 MHZ Bruker AMX-500 spectrometer at 10, 25, 50, and 80° C. Two dimensional total correlation spectroscopy (TOCSY) and nuclear Overhauser effect spectroscopy (NOESY) were performed with 256 t1 increment and 1024 complex data points in the t2 dimension. TOCSY spectra were obtained at mixing times of 40–150 milliseconds. NOESY spectra were obtained at mixing times of 60–250 milliseconds. The spectral widths were 6024 Hz in both dimensions.

RESULTS

While the [IV-H1] (SEQ ID NO:1) peptide and variants without lipid tails were not surface active, formation of monolayers at the air-water interface was observed for all investigated collagen-like peptide-amphiphiles. For (C$_{16}$)$_2$-Glu-C$_2$ and (C$_{14}$)$_2$-Glu-C$_2$ derived peptide-amphiphiles, surface pressure (which can be interpreted as a measure of resistance of amphiphile molecules against lateral compression) could be detected at surface areas of 2–3 nm$^2$/molecule (FIG. 1). The surface pressure increased gradually as the monolayer was compressed for peptide-amphiphiles containing both [IV-H1] (SEQ ID NO:1) and Gly-Pro-Hyp repeats. At a surface area of 0.6 nm$^2$/molecule no further compression was possible and the monolayer reached the maximum surface pressure and collapsed. The common value of 0.6 nm$^2$/molecule for the limiting surface area of (((C$_{16}$)$_2$-Glu-C$_2$-SEQ ID NO:2-SEQ ID NO:1) and (C$_{14}$)$_2$-Glu-C$_2$-[IV-H1]-(Gly-Pro-Hyp)$_4$ ((C$_{14}$)$_2$-Glu-C$_2$-SEQ ID NO:1-SEQ ID NO:2) peptide-amphiphiles can only be explained assuming a fully stretched, elongated peptide head group. Prior-ray crystallographic analyses of a triple-helical peptide revealed hexagonal-packed trimers with axis-to-axis distances of 1.4 nm. The calculated surface area for this triple-helical peptide would be 1.7 nm$^2$/trimer, very close to the surface area of 1.8 nm$^2$/trimer for the peptide-amphiphiles studied here.

A dependency of the π-A isotherm on the length of the dialkyl tail for the investigated peptide head groups for alkyl chains larger than C$_{14}$ was not observed. The π-A isotherms for C$_{12}$ amphiphiles repeat the trend that was observed for amphiphiles with longer alkyl chains, though monolayers of the former are not as stable at room temperature. However, good solubility in the aqueous subphase makes C$_{12}$ compounds well suited for spectroscopic investigations. Spectral observations for only the C$_{12}$ amphiphiles are reported below, but the main spectral features have been observed independent of the amphiphile tail length.

Figure 2:
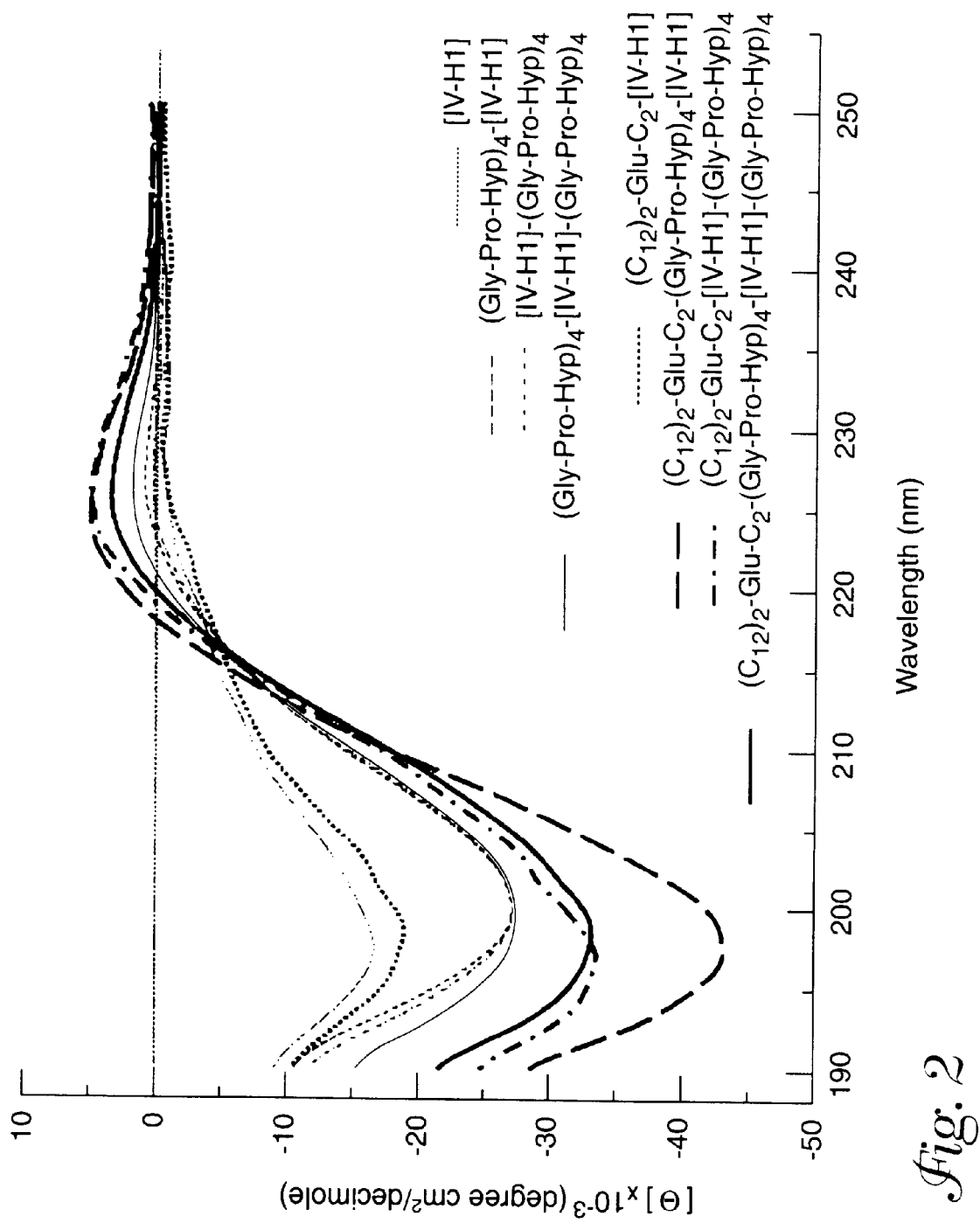
FIG. 2. Circular dichroism spectra of collagen-model peptides and peptide-amphiphiles. Positive values of ellipticity in the range λ=215–245 nm are attributed to an ordered, poly-Pro II like structure. Amongst the investigated peptides, only (Gly-Pro-HYP)$_4$-[IV-H1]-(Gly-Pro-Hyp)$_4$ SEQ ID NO:2-SEQ ID NO:1-SEQ ID NO:2) shows this structure distinctly. However, except for $(C_{12})_2$-Glu-$C_2$-[IV-H1], $((C_{12})_2$-Glu-$C_2$-SEQ ID NO:1)) all peptide-amphiphiles display a positive signal with the residual ellipticity corresponding to the maximum values reported for triple-helical structures. Solutions of $(C_{12})_2$-Glu-$C_2$-Gly (the lipid tail without a collagenous head group) show little positive or negative ellipticity over the range γ=190–250 nm (data not shown).

Collagens in triple-helical conformation exhibit a circular dichroism (CD) spectrum similar to a poly-Pro II helix, with positive ellipticity from λ=215–240 nm. At 25° C., (Gly-Pro-Hyp)$_4$-[IV-H1]-(Gly-Pro-Hyp)$_4$ (SEQ ID NO:2-SEQ ID NO:1-SEQ ID NO:2) was found to exhibit this characteristic CD spectrum (FIG. 2). For (Gly-Pro-Hyp)$_4$-[IV-H1] (SEQ ID NO:2-SEQ ID NO:1) and [IV-H1]-(Gly-Pro-Hyp)$_4$ (SEQ ID NO:1-SEQ ID NO:2) a small magnitude of positive ellipticity at λ=225 nm was observed, while the [IV-H1] (SEQ ID NO:1) peptide did not show any positive ellipticity at this wavelength. Of the peptide-amphiphiles, (C$_{12}$)$_2$-Glu-[IV-H1] ((C$_{12}$)$_2$-Glu-C$_2$-SEQ ID NO:1) displayed a CD spectrum similar to that of [IV-H1] (SEQ ID NO:1) (no positive ellipticity at λ=225 nm), while the other three amphiphiles showed a large magnitude of positive ellipticity at λ>220 nm. Most remarkably, the ellipticity per residue for the amphiphilic compounds (C$_{12}$)$_2$-Glu-C$_2$-(Gly-Pro-Hyp)$_4$-[IV-H1] ((C$_{12}$)$_2$-Glu-C$_2$-SEQ ID NO:2-SEQ ID NO:1), (C$_{12}$)$_2$-Glu-C$_2$-[IV-H1]-(Gly-Pro-Hyp)$_4$ ((C$_{12}$)$_2$-SEQ ID NO:1-SEQ ID NO:2), and (C$_{12}$)$_2$-Glu-C$_2$-(Gly-Pro-Hyp)$_4$-[IV-H1]-Gly-Pro-Hyp)$_4$ ((C$_{12}$)$_2$-Glu-C$_2$-SEQ ID NO:1-SEQ ID NO:2) was about 5 times larger than that of (Gly-Pro-Hyp)$_4$-[IV-H1]-(Gly-Pro-Hyp)$_4$ (SEQ ID NO:2-SEQ ID NO:1-SEQ ID NO:2) (FIG. 2), and approximately equal to that of (Gly-Pro-Hyp)$_{10}$ (SEQ ID NO:3). These ellipticity per residue values indicate a maximal ordered structure for (C$_{12}$)$_2$-Glu-C$_2$-(Gly-Pro-Hyp)$_4$-[IV-H1] ((C$_{12}$)$_2$-Glu-C$_2$-SEQ ID NO:2-SEQ ID NO:1), (C$_{12}$)$_2$-Glu-C$_2$-[IV-H1]-(Gly-Pro-Hyp)$_4$ ((C$_{12}$)$_2$-Glu-C$_2$-SEQ ID NO:1-SEQ ID NO:2), and (C$_{12}$)$_2$-Glu-C$_2$-(Gly-Pro-Hyp)$_4$-[IV-H1]-(Gly-Pro-Hyp)$_4$((C$_{12}$)$_2$-SEQ ID NO:2-SEQ ID NO:1-SEQ ID NO:2). It appears that all residues in these three peptide-amphiphiles are in triple-helical conformation.

Figure 3:
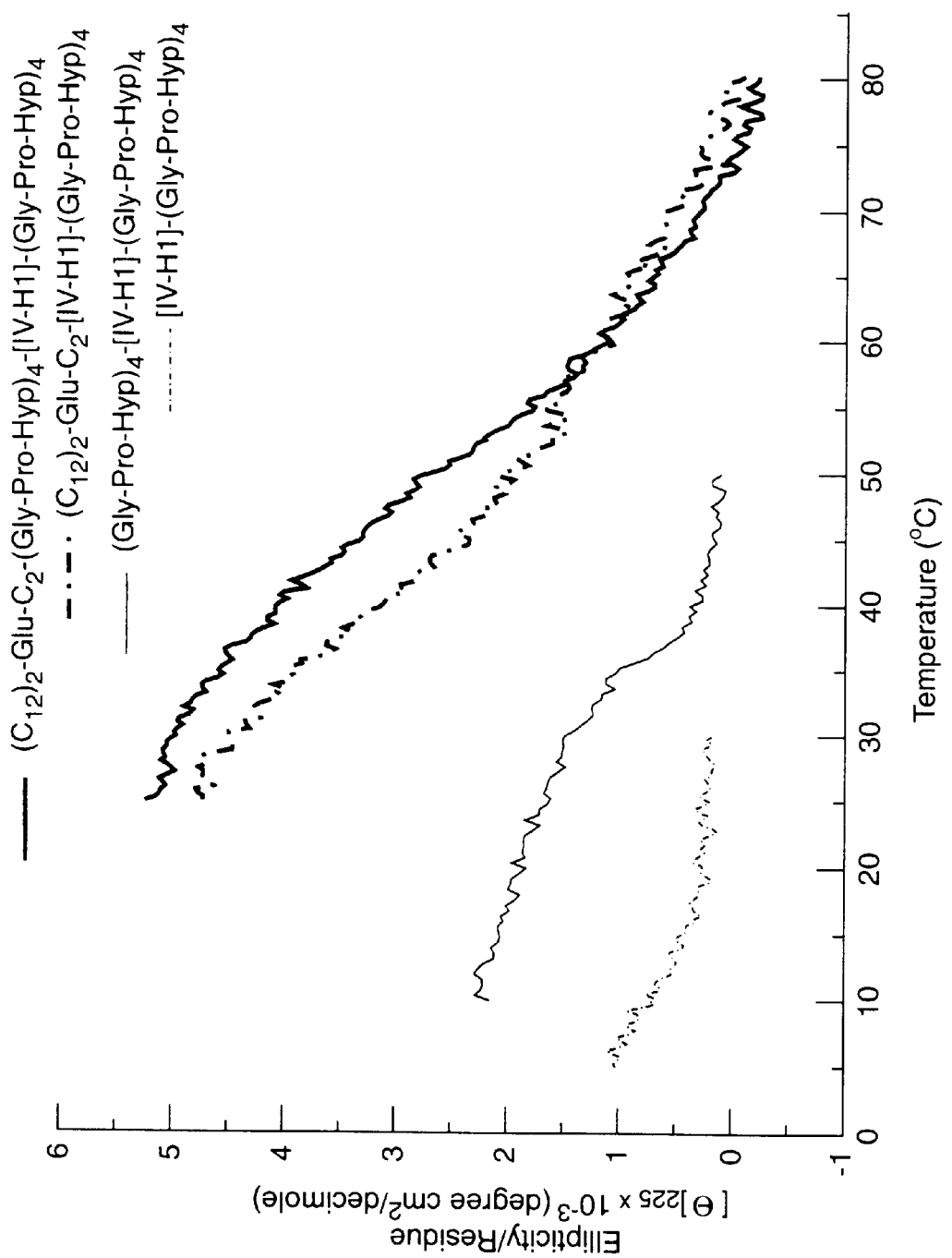
FIG. 3. Temperature dependence of circular dichroism ellipticity per amino acid residue for collagen-model peptides and peptide-amphiphiles. Amongst the peptides, only (Gly-Pro-Hyp)$_4$-[IV-H1]-(Gly-Pro-Hyp)$_4$ (SEQ ID NO:2-SEQ ID NO:1-SEQ ID NO:2) displays a thermal denaturation curve typical for collagen-like triple-helices, with a $T_m$~36° C. All peptide-amphiphiles, except $(C_{12})_2$-Glu-$C_2$-[IV-H1], $((C_{12})_2$-Glu-$C_2$-SEQ ID NO:1)) show a more gradual transition starting at 30–40° C. and finishing at about 80° C.

A triple-helical assembly can be distinguished from a simple, non-intercoiled poly-Pro II structure by its thermal denaturation behavior. A triple-helix is relatively sensitive to temperature, as it is stabilized by a hydrogen bonded intra- and inter-strand water network. Triple-helical melts are highly cooperative. The thermal stability of peptides and peptide-amphiphiles were studied by monitoring ellipticity at λ=225 nm as a function of increasing temperature. Amongst the peptides, only (Gly-Pro-Hyp)$_4$-[IV-H1]-(Gly-Pro-Hyp)$_4$ (SEQ ID NO:2-SEQ ID NO:1-SEQ ID NO:2) gave a typical sigmoidal transition associated with the transformation of triple-helical to single-stranded structure (T$_m$=36° C.) (FIG. 3). [IV-H1]-(Gly-Pro-Hyp)$_4$ (SEQ ID NO:1-SEQ ID NO:2) showed a small magnitude of positive ellipticity which decreased nearly linearly from 5–30° C. (FIG. 3), as did (Gly-Pro-Hyp)$_4$-[IV-H1] SEQ ID NO:2-SEQ ID NO:1) (data not shown). The molar ellipticities of the peptide-amphiphiles decreased gradually starting at around 30–40° C., with some traces of positive CD detectable up to 80° C. (FIG. 3). The midpoint of the transitions (T$_m$) was found to be at 50±5° C. The melting curve was fully reversible upon cooling. Although the change in ellipticity was large, thermal transitions for the peptide-aniphiphiles were broad. A broad transition is somewhat expected, as a mixture of amphiphile assemblies (monomers, micelles, vesicles, etc.) of different sizes and stabilities were melted. These observations suggest that the (Gly-Pro-Hyp)$_4$-[IV-H1]-(Gly-Pro-Hyp)$_4$ (SEQ ID NO:2-SEQ ID NO:1-SEQ ID NO:2) and (C$_{12}$)$_2$-Glu-C$_2$-(Gly-Pro-Hyp)$_4$-[IV-H1]-(Gly-Pro-Hyp)$_4$ ((C$_{12}$)$_2$-Glu-C$_2$-SEQ ID NO:2-SEQ ID NO:1-SEQ ID NO:2) structures consist of packed polyPro II-like helices, possibly triple-helical, and that the lipid tail remarkably enhanced the stability of this assembly.

The structures of the collagen-model peptides and peptide-amphiphiles were further investigated by 2D $^1$H-NMR spectroscopy. The Pro and Hyp spin systems in TOCSY were identified by the lack of amide protons and reference to the chemical shifts of the side-chain protons from other collagen-like peptides. The chemical shift of the Pro and Hyp side-chain protons was sensitive to their conformation. At 10° C., the $^1$H-NMR spectra indicated that the Pro and Hyp residues of (Gly-Pro-Hyp)$_4$-[IV-H1]-(Gly-Pro-Hyp)$_4$ (SEQ ID NO:2-SEQ ID NO:1-SEQ ID NO:2) were in a limited number of conformations, as expected for a compound with an ordered structure. The spectra of (Gly-Pro-Hyp)$_4$-[IV-H1]-(Gly-Pro-Hyp)$_4$ (SEQ ID NO:2-SEQ ID NO:1-SEQ ID NO:2) at 50° C. showed additional cross peaks at 4.85 ppm, indicating less ordered conformation at higher temperature. Some of these additional cross peaks are consistent with the multiple states that exist for the Pro residues within the [IV-H1] (SEQ ID NO:1) sequence when in a non-triple-heilcal conformation. After the (Gly-Pro-Hyp)$_4$-[IV-H1]-(Gly-Pro-Hyp)$_4$ (SEQ ID NO:2-SEQ ID NO:1-SEQ ID NO:2) peptide was lipidated with a C$_{12}$ tail, similar NMR spectra were obtained. For example, (C$_{12}$)$_2$-Glu-C$_2$-(Gly-Pro-Hyp)$_4$-[IV-H1]-(Gly-Pro-Hyp)$_4$ ((C$_{12}$)$_2$-Glu-C$_2$-SEQ ID NO:2-SEQ ID NO:1-SEQ ID NO:2) at 25° C., showed a few well defined cross peaks, indicating ordered conformation of the peptide-anphiphile. Consistent with these CD observations, the NMR spectra of (C$_{12}$)$_2$-Glu-C$_2$-(Gly-Pro-Hyp)$_4$-[IV-H1]-(Gly-Pro-Hyp)$_4$ ((C$_{12}$)$_2$-Glu-C$_2$-SEQ ID NO:2-SEQ ID NO:1-SEQ ID NO:2) at 80° C. indicated more disorder than at 25° C. Additional cross peaks were seen at 485 ppm, in similar fashion to (Gly-Pro-Hyp)$_4$-[IV-H1]-(Gly-Pro-Hyp)$_4$ (SEQ ID NO:2-SEQ ID NO:1-SEQ ID NO:2) at 50° C. Overall, the CD and NMR spectra of the (Gly-Pro-Hyp)$_4$-[IV-H1]-(Gly-Pro-Hyp)$_4$ (SEQ ID NO:2-SEQ ID NO:1-SEQ ID NO:2) peptide and the (C$_{12}$)$_2$-Glu-C$_2$-(Gly-Pro-Hyp)$_4$-[IV-H1]-(Gly-Pro-Hyp)$_4$ ((C$_{12}$)$_2$-Glu-C$_2$-(SEQ ID NO:2-SEQ ID NO:1-SEQ ID NO:2) peptide-amphiphile suggested that both spontaneously formed a well-ordered poly-Pro II-like, possibly triple-helical, structure. Similar NMR spectra were obtained for the (C$_{12}$)$_2$-Glu-C$_2$-[IV-H1]-(Gly-Pro-Hyp)$_4$ ((C$_{12}$)$_2$-Glu-C$_2$-SEQ ID NO:1-SEQ ID NO:2) and (C$_{12}$)$_2$-Glu-C$_2$-(Gly-Pro-Hyp)$_4$-[IV-H1] ((C$_{12}$)$_2$-Glu-C$_2$-SEQ ID NO:2-SEQ ID NO:1) peptide-amphiphiles.

Discussion

The lipid hydrophobic interactions of the peptide-amphiphiles exert a significant influence on collagen-model structure formation and stabilization. For example, although the [IV-H1]-(Gly-Pro-Hyp)$_4$ (SEQ ID NO:1-SEQ ID NO:2) sequence has the potential of forming a triple-helix, it was realized only in the amphiphilic compound. The triple-helix was also exceptionally stable when formed in the presence of the lipid modification. The difference in the denaturation temperatures between the structured (Gly-Pro-Hyp)$_4$-[IV-H1]-(Gly-Pro-Hyp)$_4$ (SEQ ID NO:2-SEQ ID NO:1-SEQ ID NO:2) peptide and the corresponding C$_{12}$ peptide-amphiphile was about 15–20° C. The tight alignment of the N-terminal amino acids achieved through the association of the lipid part of the molecule in a monolayer could be a simple and general tool for initiation of peptide folding. Model investigations with amphiphile monolayers mimic this general building principle. The peptide-amphiphile system presented here offers extraordinary flexibility with regard to head group geometry and macromolecular structure.

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as each were individually incorporated by reference.

---

What is claimed is:

1. A peptide-amphiphile complex comprising a lipophilic portion covalently bonded to a peptide portion at the amino-terminal end of the peptide portion, wherein the peptide portion has a super-secondary structure selected from the group of a β/α/β motif, a hairpin, and an α-helical coiled coil, and further wherein the peptide portion includes no greater than about 25 amino acid residues.

2. The complex of claim 1 wherein the peptide portion comprises one or more structure-inducing sequences.

3. The complex of claim 1 wherein the lipophilic portion comprises two linear alkyl chains.

4. The complex of claim 3 wherein each alkyl chain has up to about 20 carbon atoms.

5. The complex of claim 3 wherein the lipophilic portion further comprises a trifunctional amino acid.

6. A peptide-amphiphile complex comprising a lipophilic portion and a peptide portion, wherein the peptide portion has a secondary structure, the complex having the following structure:

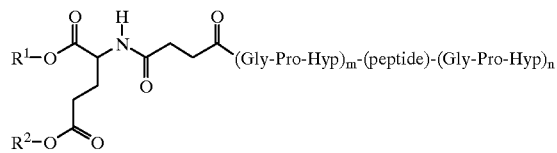

wherein:

(a) $R^1$ and $R^2$ are each independently $C_{12}$–$C_{16}$ hydrocarbyl groups;

(b) m=0–4 and n=0–4; with the proviso that at least one of m or n is 4; and (c) the (peptide) refers to the α1(IV)1263–1277 collagen sequence Gly-Val-Lys-Gly-Asp-Lys-Gly-Asn-Pro-Gly-Trp-Pro-Gly-Ala-Pro (SEQ ID NO:1).

7. A peptide-amphiphile complex comprising a lipophilic portion covalently bonded to a peptide portion, wherein the peptide portion has a secondary structure, the complex having the following structure:

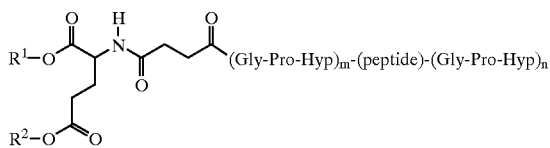

wherein:
(a) $R^1$ and $R^2$ are each independently $C_{10}$–$C_{20}$ hydrocarbyl groups;
(b) m=0–4 and n=0–4; and
(c) the (peptide) refers to the α1(IV)1263–1277 collagen sequence Gly-Val-Lys-Gly-Asp-Lys-Gly-Asn-Pro-Gly-Trp-Pro-Gly-Ala-Pro (SEQ. ID NO: 1).

8. The complex of claim 7 wherein each $R^1$ and $R^2$ are independently $C_{12}$–$C_{16}$ hydrocarbyl groups.

9. The complex of claim 7 wherein at least one of m or n is 4.

10. The complex of claim 7 which is in the form of a vesicle.

11. The complex of claim 7 which is in the form of a micelle.

12. The complex of claim 7 wherein the lipophilic portion comprises two linear alkyl chains.

13. The complex of claim 12 wherein each alkyl chain has up to about 20 carbon atoms.

14. The complex of claim 12 wherein the lipophilic portion further comprises a trifunctional amino acid.

15. The complex of claim 14 wherein the trifunctional amino acid is glutamate.

16. A peptide-amphiphile complex comprising a lipophilic portion covalently bonded to a peptide portion at the amino-terminal end of the peptide portion, wherein the peptide portion has a super-secondary structure selected from the group of a β/α/β motif, a hairpin, and an α-helical coiled coil, and further wherein the lipophilic portion comprises two linear alkyl chains and glutamate.

17. The complex of claim 16 wherein the peptide portion comprises a cell recognition site.

18. The complex of claim 16 wherein the super-secondary structure is an α-helical coiled-coil.

19. The complex of claim 16 wherein the melting temperature of the peptide portion is at least about 36° C.

20. The complex of claim 16 which is the form of a vesicle.

21. The complex of claim 16 which is in the form of a micelle.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
         (A) LENGTH: 15 amino acids
         (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:1:

Gly Val Lys Gly Asp Lys Gly Asn Pro Gly Trp Pro Gly Ala Pro
1               5                   10                  15

(2) INFORMATION FOR SEQ ID NO:2:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Gly Pro Xaa Gly Pro Xaa Gly Pro Xaa Gly Pro Xaa
1               5                   10

(2) INFORMATION FOR SEQ ID NO:3:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
        20                  25                  30
```